(12) United States Patent
Holzer (10) Patent No.: US 11,284,868 B2
(45) Date of Patent: *Mar. 29, 2022

(54) MULTI-FUNCTION DERMATOLOGICAL BIOPSY INSTRUMENT

(71) Applicant: Aton Holzer, Boca Raton, FL (US)

(72) Inventor: Aton Holzer, Boca Raton, FL (US)

( * ) Notice: Subject to any disclaimer, the term of this patent is extended or adjusted under 35 U.S.C. 154(b) by 502 days.

This patent is subject to a terminal disclaimer.

(21) Appl. No.: 16/252,772

(22) Filed: Jan. 21, 2019

(65) Prior Publication Data

US 2019/0209143 A1 Jul. 11, 2019

Related U.S. Application Data

(63) Continuation of application No. 14/817,793, filed on Aug. 4, 2015, now Pat. No. 10,182,797.

(Continued)

(51) Int. Cl.
*A61B 10/02* (2006.01)
*A61B 17/00* (2006.01)
(Continued)

(52) U.S. Cl.
CPC .... *A61B 10/0266* (2013.01); *A61B 17/00491* (2013.01); *A61B 17/064* (2013.01);
(Continued)

(58) Field of Classification Search
CPC .......... A61B 10/0266; A61B 17/00491; A61B 17/064; A61B 17/068; A61B 90/39;
(Continued)

(56) References Cited

U.S. PATENT DOCUMENTS 4,461,305 A * 7/1984 Cibley ............... A61B 10/0266
30/113.1
5,089,009 A * 2/1992 Green .................. A61B 17/064
411/457

(Continued)

FOREIGN PATENT DOCUMENTS

JP 2006087474 4/2006

OTHER PUBLICATIONS

Supplementary European Search Report for corresponding EP Appl No. 16889189.3, dated Aug. 21, 2019.
(Continued)

*Primary Examiner* — Rene T Towa
(74) *Attorney, Agent, or Firm* — Alphapatent Associates, Ltd; Daniel J. Swirsky (57) ABSTRACT

A multi-function instrument for use in a dermatological biopsy procedure, including a housing having an aperture in a base thereof, the aperture adapted to be placed on a patient's skin at a biopsy site, the housing comprising: an anesthetic-dispensing member, a biopsy sampling member configured for extracting a biopsy sample from the biopsy site, and an extension and retraction mechanism configured to enable the anesthetic-dispensing member and the biopsy sampling member to be held in offset positions relative to the aperture and to be alternately brought into alignment with the aperture for extension therethrough, to sequentially dispense an anesthetic to the selected biopsy site, and extract a biopsy sample from the biopsy site, without necessity for removal of the instrument from contact with the patient's skin.

20 Claims, 7 Drawing Sheets

Related U.S. Application Data (60) Provisional application No. 62/032,705, filed on Aug. 4, 2014.

(51) Int. Cl.
  *A61B 17/064* (2006.01)
  *A61B 17/068* (2006.01)
  *A61B 90/00* (2016.01)
  *A61B 17/06* (2006.01)

(52) U.S. Cl.
  CPC .......... *A61B 17/068* (2013.01); *A61B 90/39* (2016.02); *A61B 2010/0208* (2013.01); *A61B 2017/00004* (2013.01); *A61B 2017/0641* (2013.01); *A61B 2017/0647* (2013.01); *A61B 2017/0649* (2013.01); *A61B 2017/06176* (2013.01); *A61B 2090/395* (2016.02); *A61B 2560/0418* (2013.01)

(58) Field of Classification Search
  CPC .. A61B 2017/06176; A61B 2017/0641; A61B 2017/0647; A61B 2017/0649; A61B 2090/395; A61B 2010/0208; A61B 2560/0418; A61B 2017/00004
  See application file for complete search history.

(56) References Cited

U.S. PATENT DOCUMENTS

| | | | |
|---|---|---|---|
| 6,280,399 | B1 | 8/2001 | Rossin et al. |
| 6,547,467 | B2 * | 4/2003 | Quintero .......... A61B 17/00491 |
| | | | 206/438 |
| 2001/0034528 | A1 | 10/2001 | Foerrster et al. |
| 2002/0161298 | A1 | 10/2002 | Burbank et al. |
| 2005/0038355 | A1 | 2/2005 | Gellman et al. |
| 2005/0149092 | A1 | 7/2005 | Dunn |
| 2007/0055215 | A1 | 3/2007 | Tran et al. |
| 2009/0253997 | A1 | 10/2009 | Chen |
| 2009/0297251 | A1 * | 12/2009 | Sokoloff ................ A61B 90/39 |
| | | | 401/261 |
| 2013/0324911 | A1 | 12/2013 | Ohri et al. |
| 2014/0228708 | A1 | 8/2014 | Al Mohizea |
| 2015/0057572 | A1 | 2/2015 | Mendez-Coll et al. |

OTHER PUBLICATIONS

Japanese Office Action for corresponding JP Appl No. 2018-558505, dated Dec. 10, 2019.

* cited by examiner

MULTI-FUNCTION DERMATOLOGICAL BIOPSY INSTRUMENT

FIELD OF THE INVENTION

This invention relates to instruments used in effecting or carrying out dermatological biopsies and in particular relates to instruments providing multiple biopsy functions.

BACKGROUND

A dermatological or skin biopsy procedure, such as for determining skin cancer and the like, involves certain general procedures, which are often effected by different instruments. A typical biopsy procedure entails the initial marking of the biopsy site with a visible marker. Thereafter, the marked site is injected with a local anesthetic, typically lidocaine. A skin removal device, for the typical removal of a skin sample of between 3-5 mm is used for obtaining the sample for biopsy (most commonly 4 mm). Such skin removal devices are commonly of two types, a skin scraper for removal of a shallow skin sample, and a skin punch, which cores a skin sample of greater depth. Use of the skin punch requires further measures for wound closure such as suturing or cauterizing of the punch wound. Because of the shallower depth of skin removal by the skin scraper, wound closure with a suture may or may not be required, depending on the nature of the biopsy wound. Separate instruments are often used for each of the aforementioned procedures with complications engendered thereby. Often, the proper following of the procedures requires several people to perform the steps. This further often necessitates the need for coordination as well as proper and exact positioning of the instruments of anesthetic and biopsy removal to provide for minimal time for the procedure with the greatest accuracy in biopsy sample taking and with minimal patient pain and most effective healing measures.

In an example of the above, punch biopsy of the skin is a procedure by which dermatologists obtain tissue for histopathologic evaluation. The procedure as currently done requires several components. The dermatologist who wishes to perform the punch biopsy must incise the skin, and then drop the obtained tissue sample into an open specimen bottle. For effective handling, the dermatologist must generally have an assistant on hand to assist.

This procedure is however, not staff-efficient, since it requiring an assistant to draw anesthetic, to prepare instruments on a tray and to cut the suture. In addition, pitfalls of the current technique include often-happening occurrences wherein:

(1) the biopsy specimen detaches during the punch incision and becomes lodged in the coring blade, requiring ingenuity to remove it;
(2) when the biopsy specimen does not detach with the punch incision, removal with forceps can crush the specimen and create difficulties for the interpreting dermatopathologist for proper diagnosis.

Furthermore, the typical use of suture closures, obligates the patient to return in a week's time for suture removal, even if the pathologic diagnosis (and hence follow-up visit) may be available sooner. Although placement of an absorbable subcutaneous suture would obviate the need for this return visit, common absorbable sutures are generally impractical in the 4-mm hole created by the most common size of punch biopsy device.

SUMMARY

It is accordingly an object herein to provide a single multi-function biopsy instrument for the taking of skin samples, which permits single-person operation with increased efficiency and accuracy of coordinating anesthetic dosing and skin removal site and optionally with skin biopsy wound closure such as with suturing which does not require suture removal.

It is a further object is to provide a biopsy system that facilitates injection of anesthetic, removal and ejection of obtained biopsy specimens and wound closure by means of one disposable device, resolving many, if not all, of the inefficiencies and pitfalls of common prior art procedures.

An instrument for use in a dermatological biopsy sampling procedure as disclosed herein comprises a hand-held device comprising:

a) a member configured for effectively dispensing an anesthetic to a selected biopsy site on a patient's skin, and
b) a member configured for taking a biopsy sample from the biopsy site.

The instrument comprises a housing for the anesthetic dispensing member and biopsy sample taking member with the housing having an aperture therein adapted to be placed into contact directly against the biopsy site. The instrument comprises an extension and retraction mechanism configured to enable the anesthetic dispensing member and biopsy sample taking member to be alternately brought into proximate position relative to the selected biopsy site through the aperture. This enable the alternate and sequential providing of an anesthetic to the selected biopsy site and to take a biopsy sample from the anesthesized biopsy site, respectively, without necessity for removal of the instrument from contact with the biopsy site. This facilitates single user operation and accuracy biopsy site sampling.

In a useful embodiment the housing further contains:

i) a member configured to hold, apply and control an element for closure of a wound caused by the taking of the biopsy sample, and
ii) the extension and retraction mechanism being further configured to enable the wound closure member to be alternately, relative to the biopsy sample taking member, brought into proximate position relative to the biopsy wound through the aperture to close the wound with the element for closure A further embodiment herein comprises a single use multi-function biopsy instrument in a pen-like configuration comprising an anesthetic dispensing member with a dispensing activating element and a skin biopsy sampling member with a sample taking control element. Each of the anesthetic dispensing member and skin biopsy sampling member comprises an advancing and retracting mechanism configured for the alternating positioning and operative functioning of the anesthetic dispensing member and the skin biopsy sampling member at a single skin site without the necessity of moving the instrument out of a single position placement, for effecting the skin biopsy sampling. The single site placement of the anesthetic dispensing and the biopsy sampling ensures greater accuracy, expedited handling and reduced possibility of patient pain.

For further enhanced expediency, the instrument may also integrally contain a site marking element or marker and an integral suturing member, with the latter, in one embodiment, being provided with its own advancing and retracting mechanism and operational manipulating suturing element. The advancing and retracting mechanism of the integral suturing member, when part of the device, is further alternated with the positioning of the other functional members used in the biopsy sampling procedure.

In an embodiment of the instrument herein, the integral suturing element positions and operationally rotationally sets a surgical suture with a barbed absorbable staple configuration. In an embodiment of the instrument, the marking element is contained within a cap for the biopsy pen instrument and the anesthetic dispensing member, skin biopsy sampling member and the integral suturing member, when present, are longitudinally positioned and arranged within a cylindrical barrel having a tapered open end, similar to that of a pen, through which the respective members are extended to effect the respective functions of anesthetic delivery, skin biopsy sampling and optional suturing. Suturing, if required, may be effected by a separate suturing instrument and its inclusion in the instrument herein is desirable though not necessary.

In another embodiment of the invention a device is provided that contains:
1) a surgical marker,
2) local anesthetic syringe,
3) coring blade with an undercutting blade and ejector mechanism, and
4) an absorbable suture or staple that can be lowered into the wound.

The device described herein allows the hurried practitioner to easily perform a punch or scraping biopsy procedure without the need for assistants. It also ensures the easy removal of the specimen from the coring or scraping blade and removes the possibility of a crushed artifact. Additionally, with the integral suturing element, placement of the absorbable suture or staple obviates the need for a return visit for suture removal.

The above described instrument is used in effecting a biopsy sampling procedure in a method embodiment in which:

a dermatological biopsy sample is obtained from a patient's skin with the steps of:
a) marking a selected biopsy sampling site;
b) placing the aperture of the hand-held instrument of claim 12 in direct proximate contact with the marked selected biopsy sampling site;
c) advancing the anesthetic containing syringe needle through the aperture and injecting the marked selected biopsy site with the anesthetic;
d) without removal of the instrument from the selected biopsy site, retracting the syringe needle from the aperture and advancing the biopsy sample taking member through the aperture and cutting a biopsy skin sample from the anesthesized biopsy site;
e) retaining the biopsy skin sample for sample removal from the instrument;
f) retracting the biopsy taking member from the aperture and advancing the biopsy wound closure member through to aperture and closing the biopsy wound; and
g) removing the biopsy skin sample from the instrument either before or after the closing of the biopsy wound.

BRIEF DESCRIPTION OF THE DRAWINGS

Additional objects, features and advantages of the invention will become more evident from the following discussion and drawings in which.

DETAILED DESCRIPTION

According to some exemplary but not limiting embodiments, a multifunction pen type device for skin biopsy comprises three cartridges, which are individually selectively advanceable to the tip of the device and are substantially completely retractable into the body of the device.

In some embodiments, as described above, less than three or more than three cartridges are optionally used, with space therefor being modified, if necessary, in the instrument. In some embodiments, a pressure element is biased under spring action or other bias device to bring the respectively chosen function cartridge into the use position, and then returned into the rest or storage position by means of intermediate members.

In an embodiment, a plurality of pins which carry the different function cartridges are displaceable in the lower part of a housing. Arranged above these are swingable push rods actuable by means of pressure elements, which co-act with the respective underlying cartridge carrying pins in, for example, a diagonal or horizontal position. A displaceable pressure pin may be used for choosing, advancing and retracting the function cartridge, which is under the influence of a conical spring or other bias device arranged in a bushing threaded into the casing in operating position and in the rest position, with a control pendulum mounted on the spring longitudinally limited thereby and rotatable therein. In addition, a guide part is positioned at the forward end of the casing with a cartridge-bearing pin longitudinally displaceable in the longitudinal bores of the guide part under the influence of coil springs and provided with joints at its rear end and a locking guide ring positioned at the guide part. Other cartridge selection mechanisms may optionally be used.

In a useful embodiment, once advanced into place, each cartridge is equipped with a depressible tab that completes its function. The three cartridges include a syringe containing a local anesthetic, which can be injected by depressing its tab; a coring blade for punch biopsy, equipped with a curving blade at one lateral aspect that can be lowered via the depressible tab to incise the base of the specimen and enclose it within the coring blade, and, when subsequently raised to a height above the coring blade, enters the coring blade from above so that it can be lowered to eject the collected specimen; and a tube containing an S-shaped barbed absorbable surgical hook, or a three- (or more) armed surgical hook, or an absorbable suture or barbed helical suture that, when lowered into the wound, can be twisted and detached to achieve wound closure. Another embodiment may have, in place of the cartridge with coring and curving blades, a scoop-like blade and barrel to perform a shave biopsy, and in place of the cartridge containing the absorbable hook, a cartridge containing chemical cauterant, or cyanoacrylate glue. Another embodiment could incorporate a fourth cartridge with a tattoo needle and either permanent or temporary UV-fluorescent tattoo ink to provide a mark of the biopsy site for the purpose of future identification of the biopsy site of a skin cancer. In some embodiments, a gentian violet surgical marking pen is incorporated into the push button at the base of the device.

In operation, according to some embodiments, the user uncaps the surgical marker and uses it to draw a circle around the desired punch location. The push button is depressed, advancing the syringe of anesthetic to the tip of the device. Depression of the depressible tab of the syringe injects anesthetic into the desired site. The push button when depressed again, advances the coring blade to the tip of the device. The practitioner rotates the coring tip into the skin to create the incision, and advances the tip to its hub. Depression of the depressible tab of the coring blade cylinder to its lowermost point advances the curved blade to below the space of the coring blade, and the user rotates the device to incise the entire base of the specimen. The device is then lifted, pulling the specimen out of the skin. The user positions the device above a specimen bottle, raise the depressible tab to its highest point to position the curved blade above the coring blade, and depresses the depressible tab, pushing the flat end of the curved blade into the coring blade, to serve as a piston to eject the specimen into the bottle. The push button is then depressed for the third time, advancing the tube containing the S-shaped surgical hook. The tube is inserted into the wound, and the tab depressed to lower the surgical hook into the base of the wound. The user twists the device to close the wound, and then lifts the device off of the wound to detach the S-shaped hook, completing the biopsy and closure. In some embodiments, separate activation devices and/or push buttons may be provided for each cartridge and/or function. In an alternative embodiment, since the device is for single use, the specimen is retained in a receptacle integrated with the coring or scraping element and the receptacle is removed in toto for retrieval of the specimen in a fully intact state.

Figure 1:
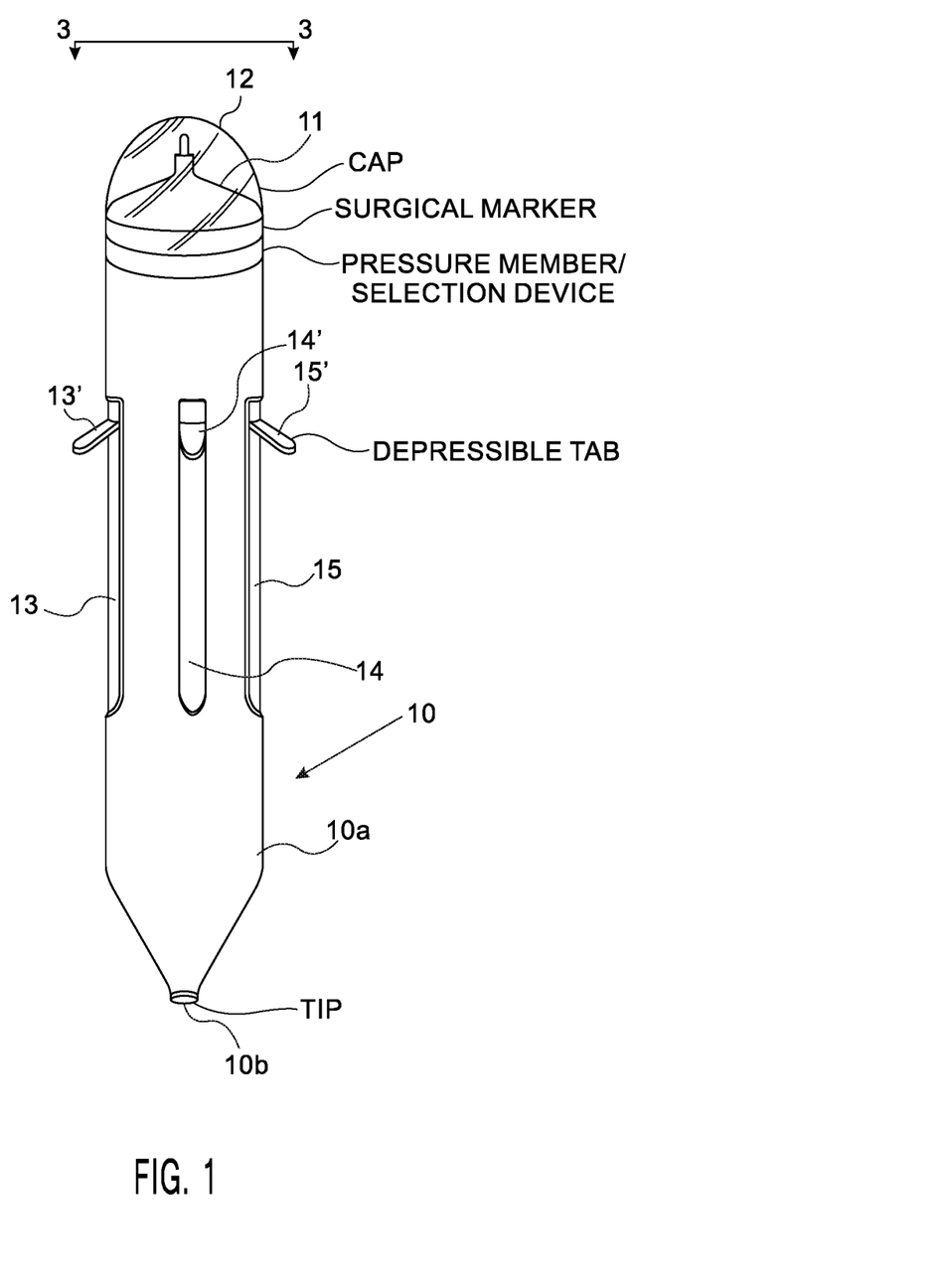
FIG. 1 is a front view of an embodiment of the multi-function biopsy instrument of the present invention with control tabs all shown in front for clarity.
Figure 2:
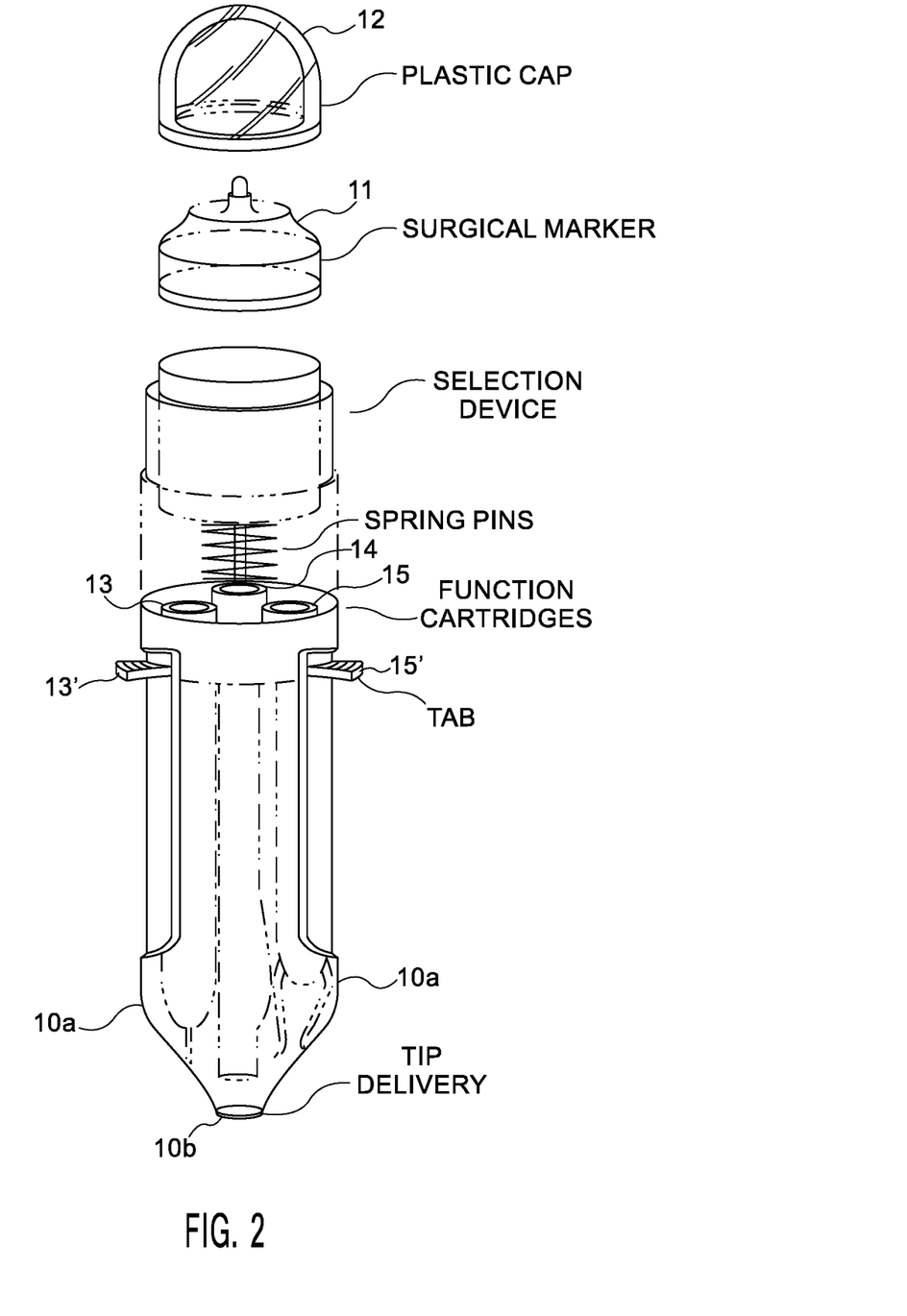
FIG. 2 is an exploded view of the multi-function biopsy instrument of FIG. 1.
Figure 3:
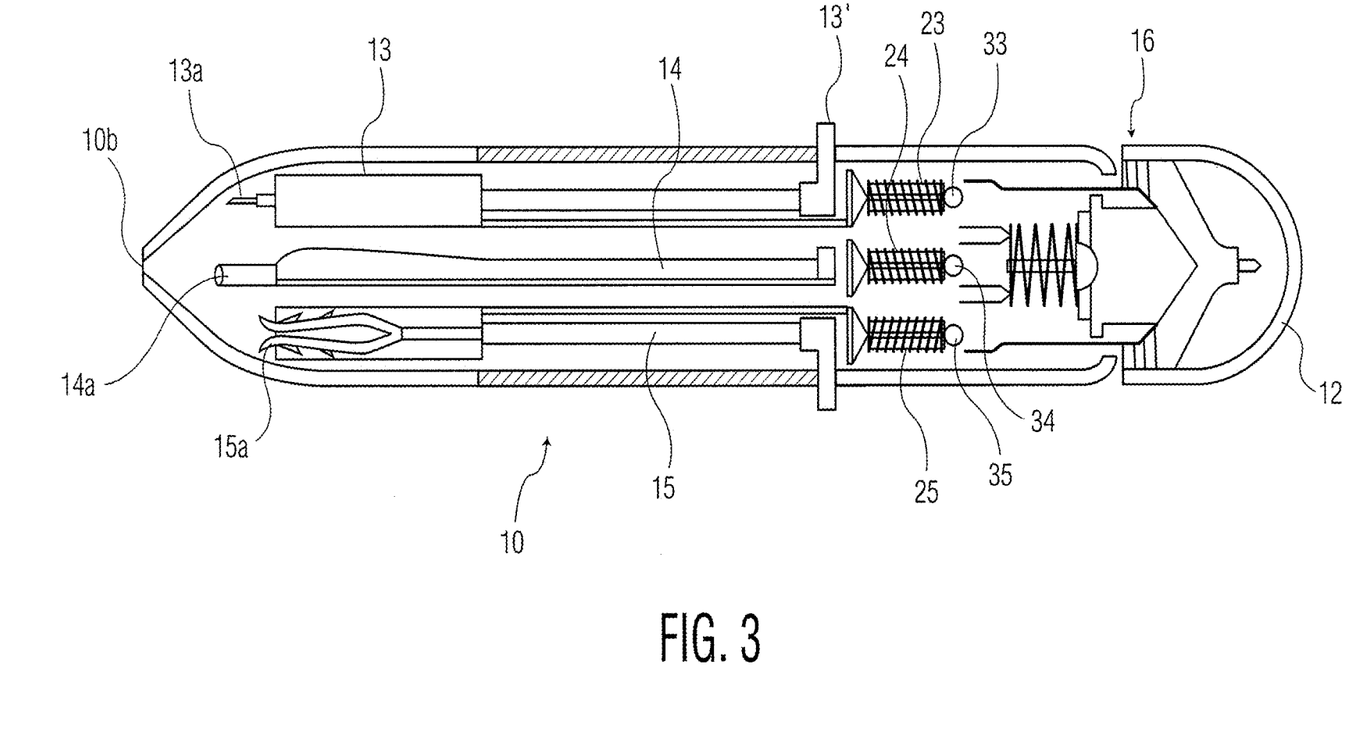
FIG. 3 is a sectioned view of the multi-function biopsy instrument of FIG. 1 taken along line 3-3.

With specific reference to the drawings, FIGS. 1-3 depict views of the biopsy pen 10, with a surgical marker 11, contained within cap 12 and in exploded and cross sectioned views respectively. The operational cartridges 13, 14 and 15; of anesthetic delivery syringe 13, biopsy sampling (coring and scraping) element 14 and suturing element 15, are longitudinally positioned within pen barrel 10a, with their operational elements (of anesthetic dispensing needle 13a; coring blade 14a, curved scraping blade 14b; and surgical suture holder 15a), being directly adjacent pen aperture tip 10b, for alternative operational extension therefrom. Logistically, the specific instrument being used is provided with either the coring or scraping blade for more specific operation control, though both biopsy removal blades may be selectively included with appropriate mechanism for selection such as with separate cartridge elements.

Figure 4:
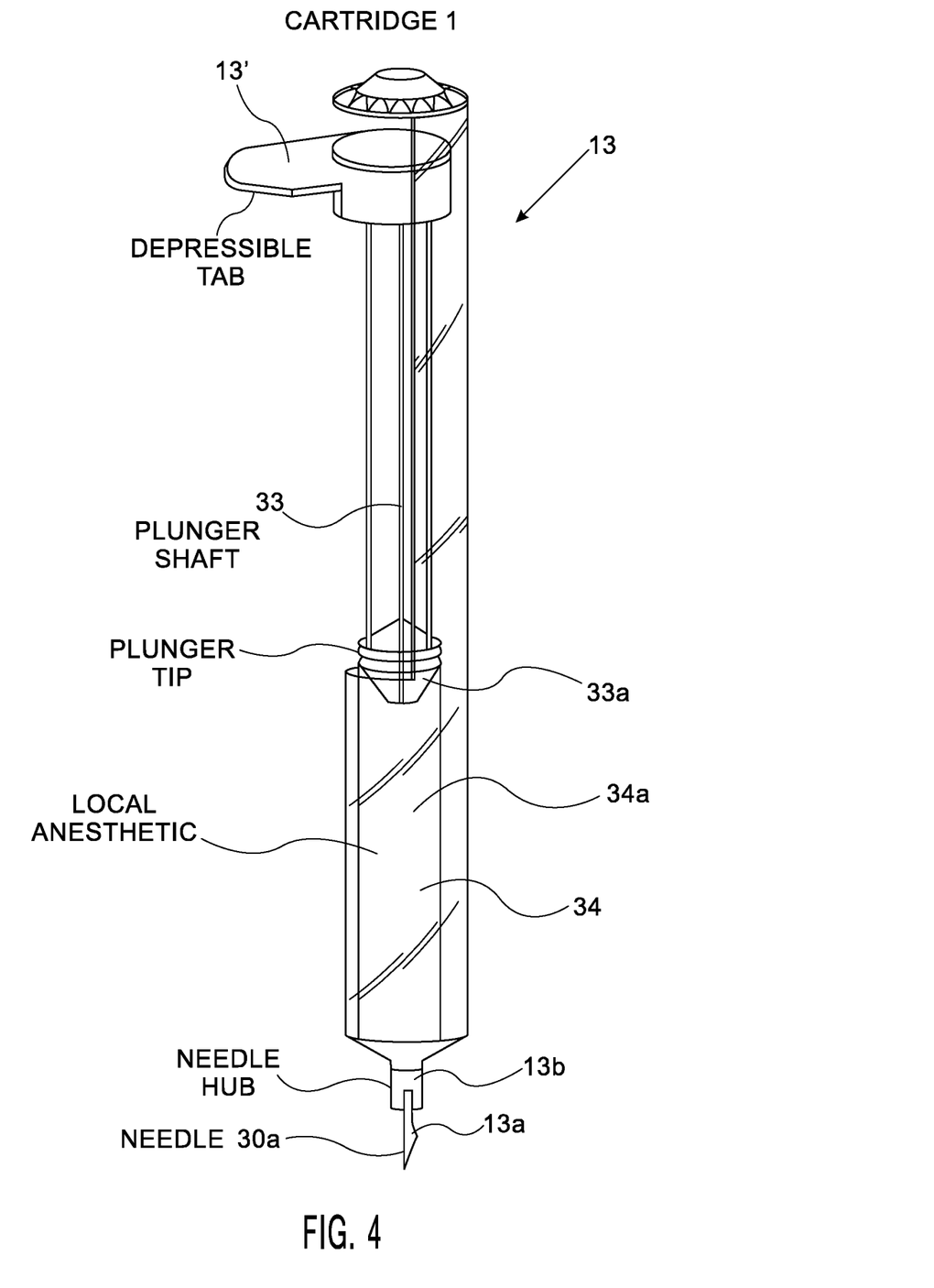
FIG. 4 is a front perspective view of the anesthetic delivery cartridge shown in FIGS. 2 and 3, taken apart from the instrument.
Figure 5A:
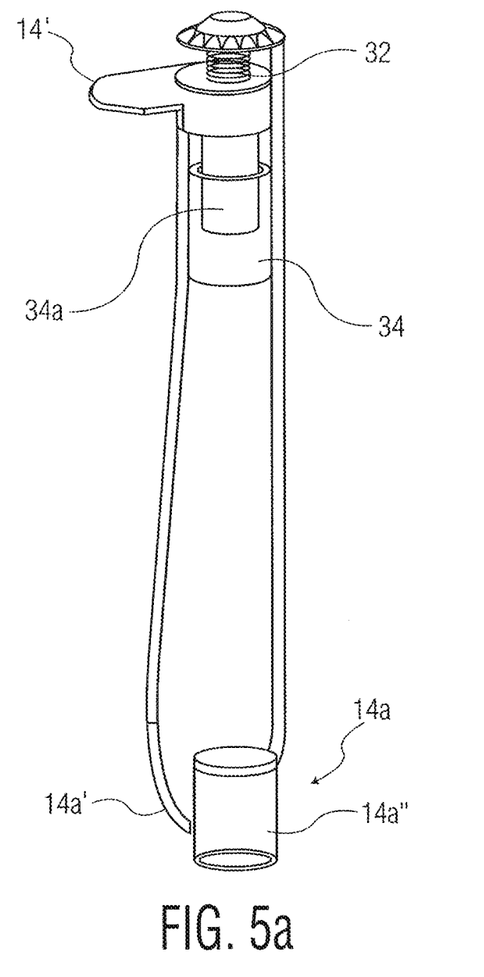
FIGS. 5*a* and 5*b* is a front perspective view of the skin biopsy sampling cartridge shown in FIGS. 2 and 3, taken apart from the instrument with FIG. 5*a* showing a coring blade and FIG. 5*b* showing an alternative operational shave blade.
Figure 5B:
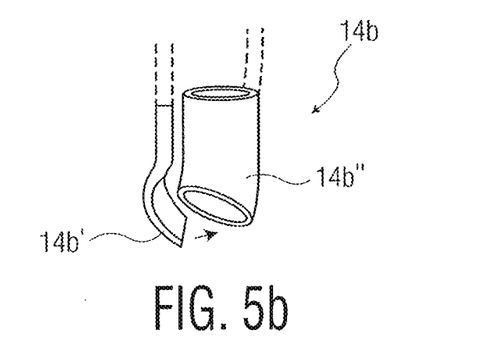
Figures 6, 7A, 7B, 7C, 7D:
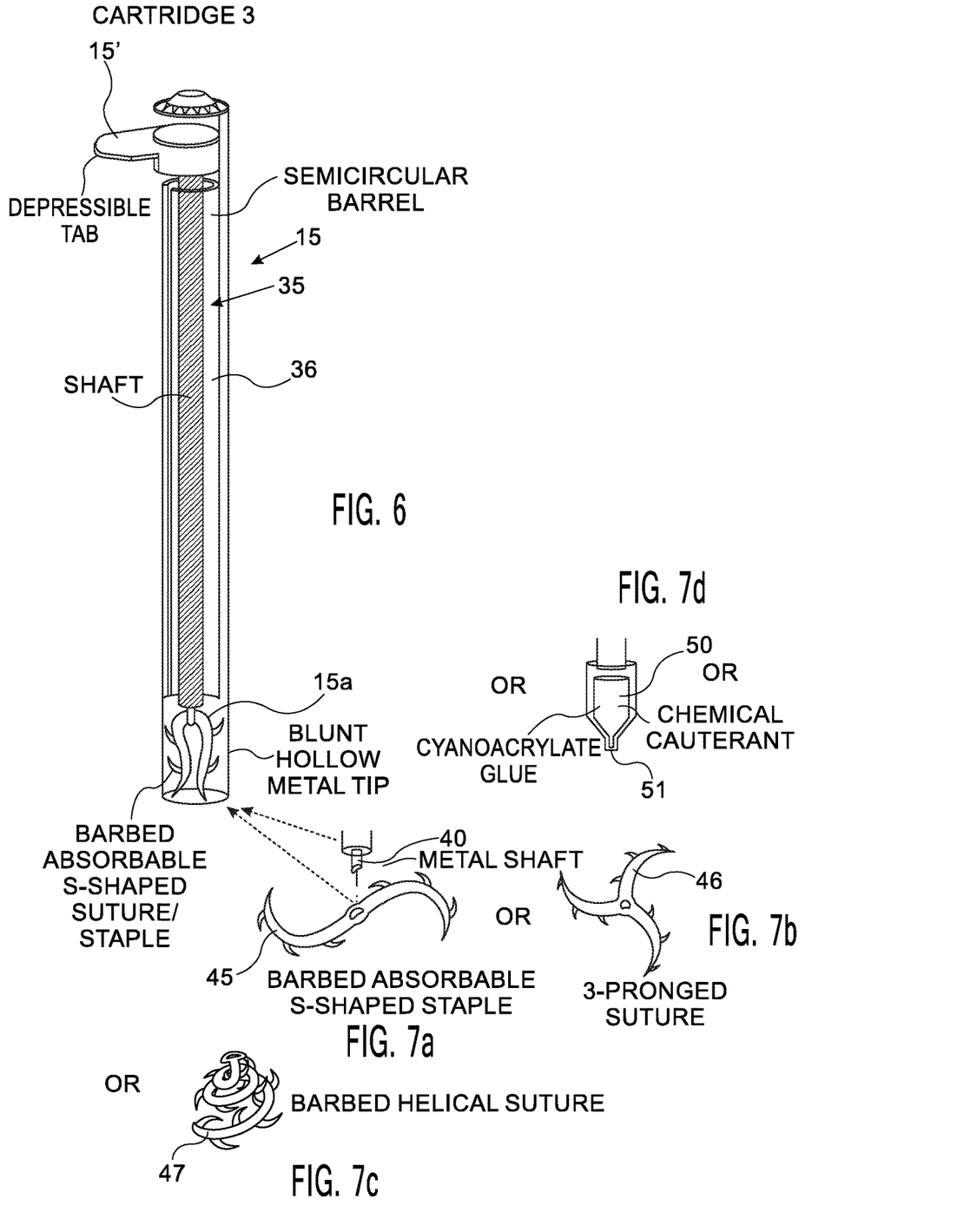
FIG. 6 is a front perspective view of the suturing cartridge shown in FIGS. 2 and 3, taken apart from the instrument.
FIGS. 7*a-d* are suturing alternatives of an s-shaped barbed absorbable staple, a three pronged suture, a barbed helical suture, and a cyanoacrylate glue dispenser or chemical cauterant, as used with or integrated with the suturing cartridge tip of the suturing cartridge of FIG. 6.

The pen barrel 10a is further provided with cartridge selection control device 16 for selection and extension/retraction control of the cartridge appropriate for a desired function. Control tabs 13', 14' and 15', integrated with cartridges 13, 14 and 15 respectively (as shown in FIGS. 4, 5, and 6 respectively), serve to effect the appropriate function of the desired cartridges (injection, scraping or coring, and suturing). Internal springs 23, 24 and 25 with pins 33, 34, and 35 for cartridges 13, 14 and 15 respectively provide requisite position and operation tension forces for the extension/retraction of the selected respective cartridges.

For the selective positioning of the operation tips 13a, 14a and 14b and 15a, they are held in an offset position relative to the aperture tip 10b until extended for use and with such extension are moved into alignment with the aperture tip 10b and therethrough for effecting the designated function.

FIG. 4 depicts the anesthetic needle dispenser cartridge 13, apart from the pen structure, with control tab 13', plunger shaft 33, plunger tip 33a, anesthetic ampoule 34 with contained anesthetic 34a, needle hub 13b and needle 13a.

FIGS. 5a and 5b show the biopsy sample obtaining structure 14, with spring 32, plunger barrel 34 and plunger tip 34a and control tab 14'. The biopsy tip 14a in FIG. 5a comprises a curved blade 14a' and coring blade 14a". The biopsy tip 14b in FIG. 5b shows the alternative shave biopsy mechanism with sharp scoop blade 14b' and blunt edge receptacle 14b".

The optional suturing cartridge 15 is shown in FIG. 6 with control tab 15' driving shaft 35 longitudinally contained and movable within semicircular barrel 36 to operate blunt hollow tip 15a engaged with one of barbed absorbable sutures shown in FIG. 7a (s-shaped staple 45), FIG. 7b (3-pronged suture 46) and FIG. 7c (barbed helical suture 47) via metal shaft connector 40 of hollow tip 15a for rotational suturing deployment to close a biopsy wound. Alternatively, tip 15a is shaped with a small ampoule configuration 50 containing a medical grade cyanoacrylate glue or chemical cauterant which is dispensed on the biopsy wound site through dispensing tip 51 to effect a biopsy wound closure without sutures.

Figure 8:
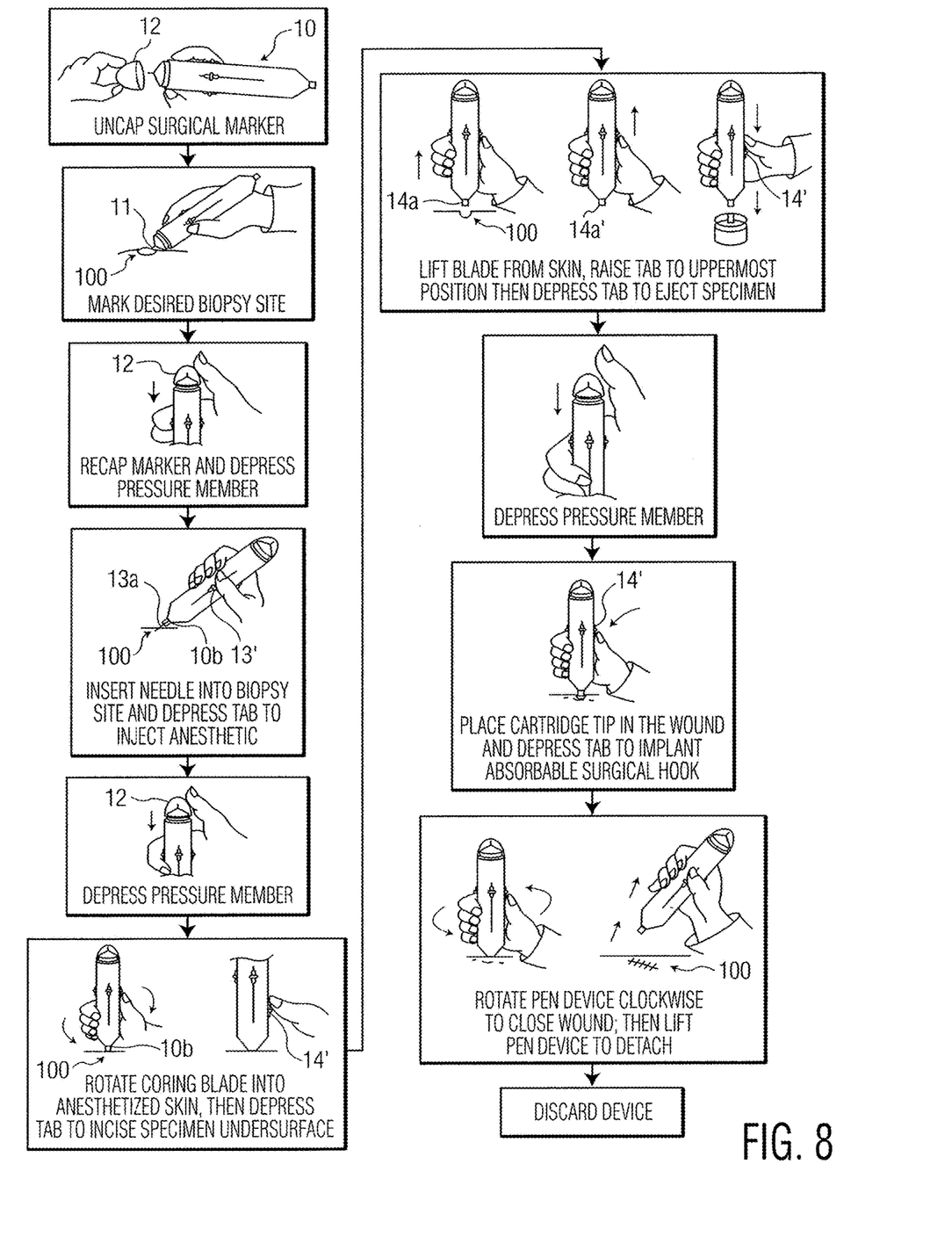
FIG. 8 is an illustrated flow chart showing the procedure of using the multi-function instrument of FIGS. 1-3 in effecting a biopsy sampling use.

As shown in illustrated flow chart of FIG. 8 of an operational procedure utilizing the biopsy instrument 10, the cap 12 is initially removed at A and the marker 11 is used to mark (with a small diameter circle) the biopsy site 100 at B. Thereafter, with the cap 12 having been replaced the cap is pressed at C to depress an internally contained pressure member, which initially causes the needle 13a of the anesthetic dispensing cartridge 13 to operationally extend out of tip opening 10b at D and the needle 13a is positioned into the marked biopsy site and tab 13' is depressed to inject anesthetic into the biopsy site 100.

Without lifting the instrument 10 from against the biopsy site 100, the cap 12 is then pressed again at E to depress the pressure member. This causes the biopsy-sampling cartridge 14 to move into position at F and in turn causes the tip 14a (with either coring tip 14a' or shaving tip 14a") to extend into engagement with the biopsy site 100. The biopsy instrument 10 is then rotated at G for coring or shaving and then the tab 14' is depressed to effect the coring or shaving incision under or on the skin surface at the biopsy site 100. Raising of tab 14' at H lifts the biopsy sample from the biopsy site with the sample being retained within the coring blade 14a" or blunt edge receptacle 14b" with the biopsy instrument 10 being lifted from the biopsy site 100. Depression of tab 14' thereafter, as shown, ejects the specimen for collection within receptacle 101.

To complete the procedure the biopsy instrument 10 is repositioned on the biopsy wound the cap 12 is again pressed to depress the pressure member at I to bring the suturing cartridge 15 into position and operative extension with suturing tip 15a. Tab 15' is depressed to implant the absorbable suturing staple (45, 46, or 47) or to dispense the cyanoacrylate glue or cauterant. The biopsy instrument 10 is then rotated to close the wound with any of the surgical staples, glue or cauterant and the biopsy instrument is lifter to detach it from the staple, glue or cauterant and the biopsy instrument is then discarded.

In another embodiment, ejection of the biopsy sample need not be made prior to the suturing step, with the biopsy instrument remaining in position against the biopsy site and wound 100 until after the suturing or wound closure has been effected and the biopsy sample being harvested with removal of the biopsy sample cartridge 14 and removal of the contained sample therefrom.

It is understood that the above description and drawings are merely illustrative of embodiments herein and that changes may be made in structure of the biopsy instrument and procedure for use thereof without departing from the scope of the invention except as defined in the following claims.

What is claimed is:

1. A multi-function instrument for use in a dermatological biopsy procedure comprising:
    a housing having an aperture in a base thereof, said aperture adapted to be placed on a patient's skin at a biopsy site, said housing comprising:
    an anesthetic-dispensing member;
    a biopsy sampling member configured for extracting a biopsy sample from said biopsy site; and
    an extension and retraction mechanism configured to hold said anesthetic-dispensing member and said biopsy sampling member in offset positions relative to the aperture and alternately move said members laterally into alignment with said aperture for extension therethrough, to sequentially dispense an anesthetic to the selected biopsy site, and extract a biopsy sample from the biopsy site, without necessity for removal of the instrument from contact with the patient's skin.

2. The biopsy sampling instrument of claim 1, wherein the anesthetic-dispensing member comprises a syringe containing an anesthetic and is configured to insert the syringe into the biopsy site and dispense the anesthetic therein.

3. The biopsy sampling instrument of claim 2, wherein said syringe is pre-filled with a specific concentration and volume of anesthetic adapted to an individual patient's requirements.

4. The biopsy sampling instrument of claim 1, wherein said biopsy sampling member comprises a biopsy coring punch configured to punch into the biopsy site to separate a core sample from the biopsy site, and a sample retention element from which the core sample is retrieved.

5. The biopsy sampling instrument of claim 1, wherein said biopsy sampling member comprises a biopsy scraping element configured to separate a skin sample from the biopsy site, and a sample retention element into which the skin sample is moved and from which the skin sample is retrieved.

6. The biopsy sampling instrument of claim 1, wherein the housing further comprises an elongated, hand-held configuration having a marking element affixed thereto, said marking element configured to mark the biopsy site.

7. The biopsy instrument of claim 1, wherein the housing comprises external finger and hand controls for selectively operating the extending and retracting mechanism and for effecting the anesthetic dispensing and biopsy sampling.

8. The biopsy instrument of claim 1, wherein the housing further comprises a wound closure member configured for closing the biopsy wound.

9. A multi-function instrument for use in a dermatological biopsy procedure comprising:
    a housing having an aperture in a base thereof, said aperture adapted to be placed on a patient's skin at a biopsy site, said housing comprising:
    a biopsy sampling member configured for extracting a biopsy sample from said biopsy site;
    a wound closure member configured for closing a wound caused by said biopsy sampling member; and
    an extension and retraction mechanism configured to hold said biopsy-sampling member and said wound closure member in offset positions relative to the aperture and alternately move said members laterally into alignment with said aperture for extension therethrough, to sequentially extract a biopsy sample from the biopsy site, and close said wound, without necessity for removal of the instrument from contact with the patient's skin.

10. The biopsy sampling instrument of claim 9, wherein the wound closure member is adapted to release one of an absorbable suture staple, a medical grade glue and a cauterant.

11. The biopsy sampling instrument of claim 10, wherein the absorbable suture staple is barbed and has at least one of an s-shape, a helical shape and a three pronged shape, such that the wound closure member holds the suture staple and carries it through the aperture to the biopsy wound.

12. The biopsy sampling instrument of claim 9, wherein the wound closure member comprises an apertured receptacle containing a sealant such as a medical grade glue or a cauterant, such that said wound closure member is configured to dispense said sealant from said apertured receptacle onto the biopsy wound for closure thereof.

13. The biopsy sampling instrument of claim 9, wherein said biopsy sampling member comprises a biopsy coring punch configured to punch into the biopsy site to separate a core sample from the biopsy site, and a sample retention element from which the core sample is retrieved.

14. The biopsy sampling instrument of claim 9, wherein said biopsy sampling member comprises a biopsy scraping element configured to separate a skin sample from the biopsy site, and a sample retention element into which the skin sample is moved and from which the skin sample is retrieved.

15. The biopsy sampling instrument of claim 9, wherein the housing further comprises an elongated, hand-held configuration having a marking element affixed thereto, said marking element configured to mark the biopsy site for application of anesthetic and for biopsy sampling thereof.

16. The biopsy instrument of claim 9, wherein the housing comprises external finger and hand controls for selectively operating the extending and retracting mechanism and for effecting the anesthetic dispensing and biopsy sampling.

17. The biopsy instrument of claim 9, wherein the housing further comprises an anesthetic-dispensing member for anesthetizing the biopsy site prior to extracting the biopsy sample.

18. A method for obtaining a dermatological biopsy sample from a patient's skin, comprising the steps of:
    a) providing a hand-held instrument having a housing with an aperture in a base thereof, said aperture adapted to be placed on a patient's skin at a biopsy site, said housing comprising:
    an anesthetic-dispensing member;
    a biopsy-sampling member; and
    an extension and retraction mechanism for said members, configured to hold said members in offset positions relative to the aperture and alternately move said members laterally into alignment with said aperture for extension therethrough;

b) placing said aperture of said hand-held instrument in direct contact with a selected biopsy sampling site;

c) advancing said anesthetic-dispensing member through the aperture and injecting said selected biopsy site with the anesthetic; d) without removal of the instrument from the selected biopsy site, retracting the anesthetic-dispensing member from the aperture and advancing the biopsy sampling member through the aperture, and cutting a biopsy skin sample from the anesthetized biopsy site;

e) without removal of the instrument from the selected biopsy site, retracting said biopsy sampling member, thereby extracting the cut biopsy sample away from the underlying tissue; and f) removing the instrument from the biopsy site, and removing the extracted biopsy sample from the instrument, wherein steps c), d) and e) are performed using said extension and retraction mechanism such that said members are held in offset positions relative to the aperture and are alternately moved laterally into alignment with said aperture during extension therethrough.

19. A method according to claim 18, wherein a marking element incorporated within said housing is used to mark said biopsy site prior to placing said aperture of said hand-held instrument in direct contact with a selected biopsy sampling site.

20. A method according to claim 18, further comprising a step of deploying a wound closure member incorporated within said housing to close the biopsy wound.

* * * * *